United States Patent
Maeda

(10) Patent No.: US 8,892,254 B2
(45) Date of Patent: Nov. 18, 2014

(54) ROBOT CONTROLLER AND ROBOT SYSTEM

(71) Applicant: Kabushiki Kaisha Yaskawa Denki, Kitakyushu (JP)

(72) Inventor: Takahiro Maeda, Fukuoka (JP)

(73) Assignee: Kabushiki Kaisha Yaskawa Denki, Kitakyushu-Shi (JP)

( * ) Notice: Subject to any disclaimer, the term of this patent is extended or adjusted under 35 U.S.C. 154(b) by 101 days.

(21) Appl. No.: 13/759,050

(22) Filed: Feb. 5, 2013

(65) Prior Publication Data

US 2014/0114476 A1    Apr. 24, 2014

(30) Foreign Application Priority Data

Oct. 22, 2012  (JP) ................................. 2012-233181

(51) Int. Cl.
*G06F 19/00* (2011.01)
*B25J 9/16* (2006.01)
*G05B 19/418* (2006.01)
*G01N 1/31* (2006.01)

(52) U.S. Cl.
CPC .............. *G05B 19/418* (2013.01); *G01N 1/312* (2013.01); *B25J 9/1682* (2013.01)
USPC ............. 700/248; 700/245; 700/250; 422/63; 422/65; 435/286.4; 435/287.3

(58) Field of Classification Search
CPC .............. G01N 35/0092; G01N 1/312; G01N 35/0099; G01N 1/31; G06F 19/3406
USPC ...................... 700/245, 248, 250; 422/63, 65; 435/286.4, 287.3
See application file for complete search history.

(56) References Cited

U.S. PATENT DOCUMENTS

| | | | |
|---|---|---|---|
| 5,204,942 A * | 4/1993 | Otera et al. | 700/248 |
| 5,429,682 A * | 7/1995 | Harlow et al. | 118/681 |
| 5,519,814 A * | 5/1996 | Rodriguez et al. | 700/264 |
| 5,645,884 A * | 7/1997 | Harlow et al. | 427/8 |
| 7,525,274 B2 * | 4/2009 | Kazi et al. | 318/568.1 |

(Continued)

FOREIGN PATENT DOCUMENTS

| | | |
|---|---|---|
| JP | 03-182908 | 8/1991 |
| JP | 2011-233071 | 11/2011 |
| JP | 2012-183640 | 9/2012 |

OTHER PUBLICATIONS

Japanese Office Action for corresponding JP Application No. 2012-233181, Jan. 21, 2014.

*Primary Examiner* — McDieunel Marc
(74) *Attorney, Agent, or Firm* — Mori & Ward, LLP

(57) ABSTRACT

A robot controller includes queues, a storage unit, and an execution control unit. The queues are provided for respective controlled groups serving as controlled units. The storage unit stores therein instructions directed to the respective controlled groups, one at a time, from a bottom end of each of the queues. When having accepted a predetermined operation request, the execution control unit simultaneously fetches the instructions directed to the controlled groups, one for each of the controlled groups at a time, from tops of the queues, and makes all of the controlled groups simultaneously start the operations based on such instructions. If there is any controlled group to which no corresponding instruction exists, the storage unit stores therein a no-operation instruction. If the fetched instruction is the no-operation instruction, the execution control unit keeps the controlled group from operating until an instruction is fetched next time.

11 Claims, 15 Drawing Sheets

(56) References Cited

U.S. PATENT DOCUMENTS

| | | | |
|---|---|---|---|
| 7,558,646 B2* | 7/2009 | Matsumoto et al. | 700/249 |
| 7,860,609 B2* | 12/2010 | Yanagita et al. | 700/245 |
| 8,315,736 B2* | 11/2012 | Kalbavi et al. | 700/250 |
| 2006/0287769 A1* | 12/2006 | Yanagita et al. | 700/245 |
| 2009/0271034 A1* | 10/2009 | Kalbavi et al. | 700/245 |
| 2014/0142754 A1* | 5/2014 | Dai et al. | 700/245 |

* cited by examiner

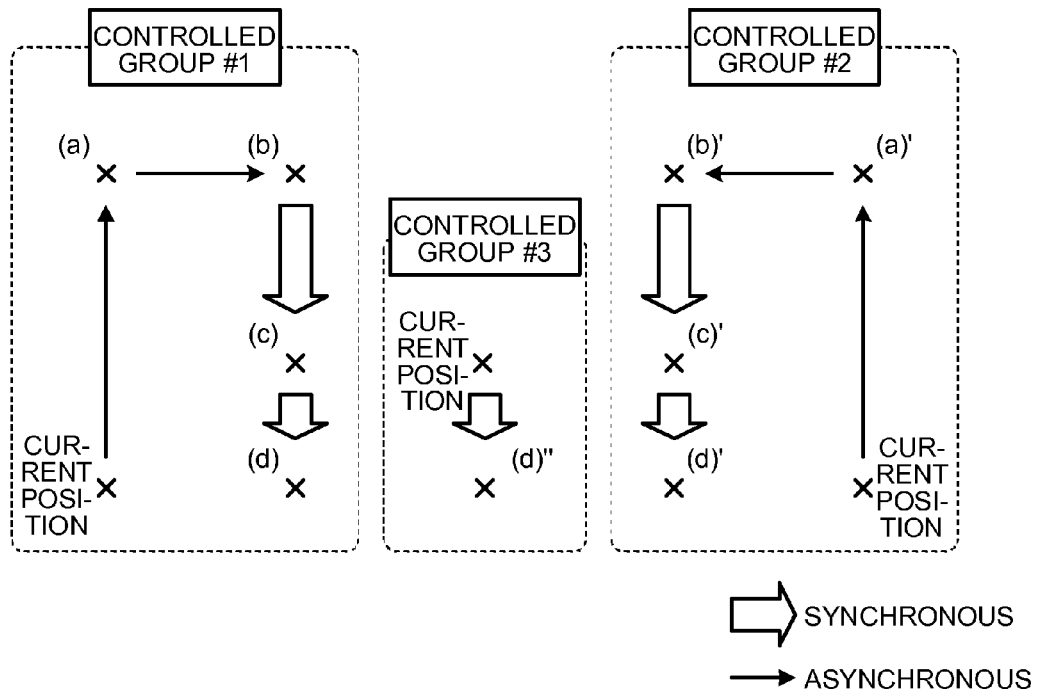

FIG.7C

| (4) | (3) | (2) | (1) | |
|---|---|---|---|---|
|  | NOP | 0 | 0 | CONTROLLED GROUP #1 |
|  | NOP | 0 | 0 | CONTROLLED GROUP #2 |
|  | 1 | NOP | NOP | CONTROLLED GROUP #3 |

ROBOT CONTROLLER AND ROBOT SYSTEM

CROSS-REFERENCE TO RELATED APPLICATION

This application is based upon and claims the benefit of priority of the prior Japanese Patent Application No. 2012-233181, filed on Oct. 22, 2012, the entire contents of which are incorporated herein by reference.

FIELD

The embodiment discussed herein is directed to a robot controller and a robot system.

BACKGROUND

There are conventionally known robot controllers, each of which is connected to a plurality of robots in a mutually communicable manner and individually controls operations of each of the robots (refer, for example, to Japanese Patent Application Laid-open No. H3-182908).

Such a robot controller has, for example, first-in first-out buffers, each assigned to each of the robots, and can operate the robots in parallel by sequentially reading instructions directed to each of the robots stored in each of the buffers and by executing the instructions.

The robot controller can include, as controlled objects thereof, peripheral devices or the like of the robots, in addition to the robots themselves. In such cases, the robot controller treats each of the robots and the peripheral devices thereof as one controlled unit (hereinafter mentioned as "controlled group"), and controls operations of each of such controlled groups.

However, conventional robot controllers and robot systems provided therewith have insufficient synchronization accuracy between controlled groups, and therefore, are yet to be further improved in making the controlled groups perform coordinated operations in synchronization with each other.

SUMMARY

A robot controller according to an aspect of an embodiment includes queues, a storage unit, and an execution control unit. The queues are provided for respective controlled groups serving as controlled units each including at least one axis of movement involved in an operation of robots. The storage unit stores therein instructions directed to the respective controlled groups, one at a time, from a bottom end of each of the queues. When having accepted a predetermined operation request, the execution control unit simultaneously fetches the instructions directed to the controlled groups, one for each of the controlled groups at a time, from tops of the queues, and makes all of the controlled groups simultaneously start the operations based on such instructions. If there is any controlled group to which no corresponding instruction exists at the time of storing the instructions, the storage unit stores therein a no-operation instruction as an instruction directed to the controlled group. If the fetched instruction is the no-operation instruction, the execution control unit keeps the controlled group corresponding to the no-operation instruction from operating until an instruction is fetched next time.

BRIEF DESCRIPTION OF DRAWINGS

A more complete appreciation of the invention and many of the attendant advantages thereof will be readily obtained as the same becomes better understood by reference to the following detailed description when considered in connection with the accompanying drawings, wherein:

FIGS. 7A to 7C are diagrams (No. 1) to (No. 3) illustrating specific examples of the execution control in the robot controller according to the embodiment.

DESCRIPTION OF EMBODIMENT

An embodiment of a robot controller and a robot system disclosed herein will be described below in detail with reference to the accompanying drawings. Note that the embodiment is not limited to the embodiment illustrated below.

In the description below, each of a plurality of components of the same type is assigned with a symbol attached with a suffix in the form of a hyphen followed by a number. However, when the components are explained as a whole, they may be, in some cases, explained by using only the symbol without using such a suffix in the form of a hyphen followed by a number.

Figure 1:
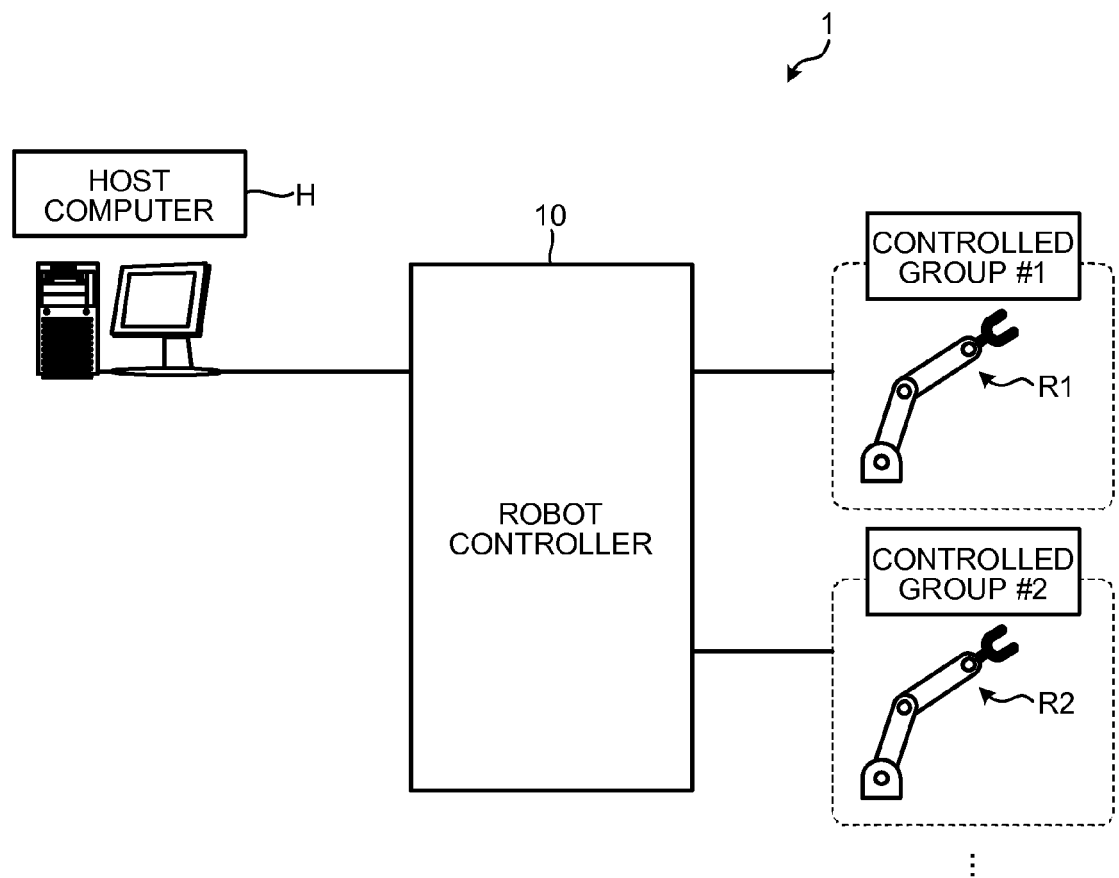
FIG. 1 is a diagram illustrating an example of an overall configuration of a robot system according to the embodiment.

First, an example of an overall configuration of a robot system 1 will be described using FIG. 1. FIG. 1 is a diagram illustrating the example of the overall configuration of the robot system 1 according to the embodiment.

As illustrated in FIG. 1, the robot system 1 is provided with a host computer H, a robot controller 10, and a plurality of controlled groups. The host computer H and the controlled groups are connected to the robot controller 10 in a mutually communicable manner.

In FIG. 1, as an example, the controlled groups that operate based on instructions generated in the host computer H are illustrated as controlled groups #1 and #2. Unless otherwise specified, the description of the present embodiment will be based on the overall configuration of FIG. 1.

The host computer H generates instructions directed to the controlled groups #1 and #2, and sends the instructions to the robot controller 10.

For example, the host computer H may be composed of a personal computer (PC), and may generate the instructions directed to the controlled groups #1 and #2 based on a description in C language. Alternatively, for example, the host computer H may be composed of a programmable logic controller (PLC), and may generate the instructions directed to the controlled groups #1 and #2 based on a description in a ladder language.

The controlled groups #1 and #2 are controlled units each having at least one axis of movement. In FIG. 1, the controlled groups #1 and #2 are composed of a robot R1 and a robot R2, respectively. Peripheral devices (not illustrated) or the like other than the robot can each form a controlled group as far as the peripheral devices or the like are controlled by the robot controller. As the peripheral devices, there can be exemplified a mobile platform that mounts thereon and horizontally moves the robot, and a turntable that changes a direction of an object so that the robot can easily work on the object. Each of such peripheral devices forms an individual controlled group. However, the description below assumes that each of the controlled groups is composed of one robot.

The robot controller 10 receives the instructions sent out from the host computer H to the controlled groups #1 and #2, and stores each of the instructions in a predetermined storage area provided in advance for each of the controlled groups. Note that each of the instructions may be attached with information for identifying to which of the controlled groups the instruction is directed, and may be stored in a common storage area. When sending out the instructions, the host computer H sends out a "no-operation instruction" to a controlled group to which no instruction to be executed is to be issued. Hereinafter, such a "no-operation instruction" may be mentioned as "NOP". The robot controller 10 also sequentially fetches the stored instructions, and performs execution control so that the controlled groups #1 and #2 perform coordinated operations while being accurately synchronized.

Figure 2:
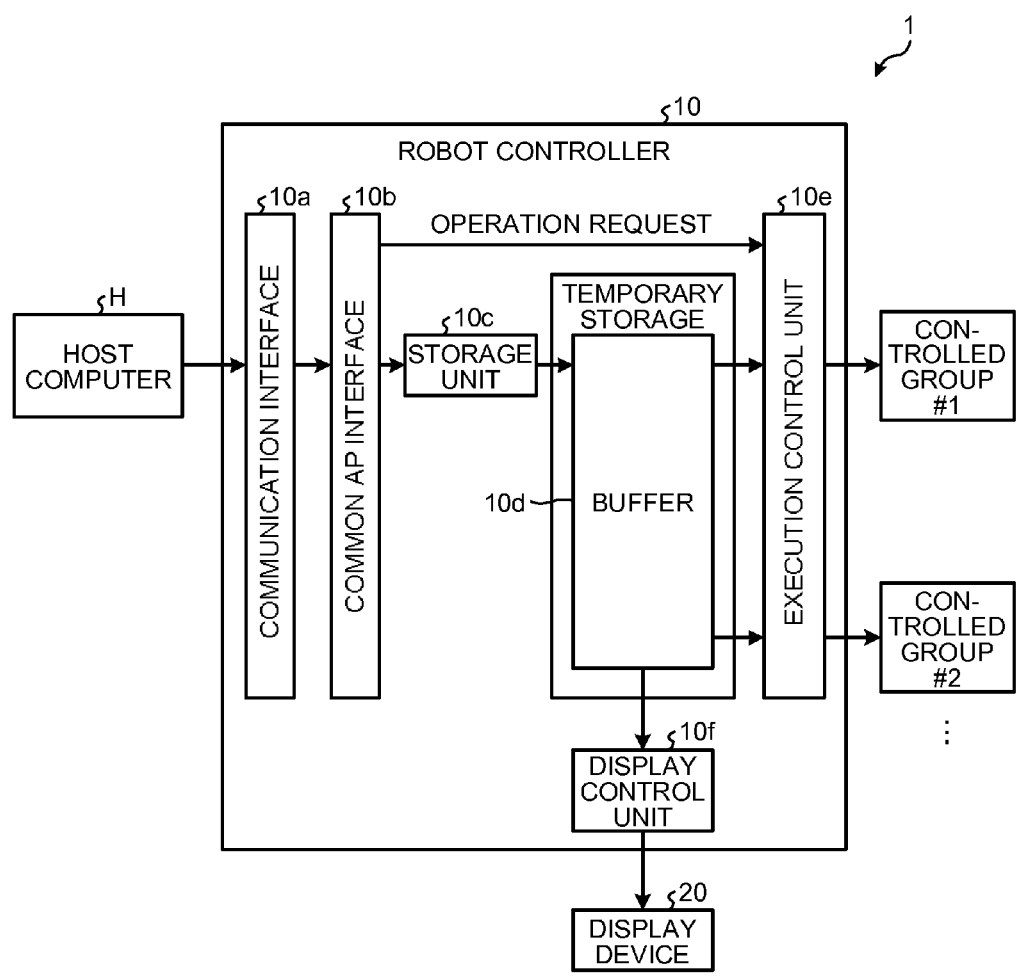
FIG. 2 is a block diagram illustrating a configuration of a robot controller according to the embodiment.

Next, a configuration of the robot controller 10 will be described using FIG. 2. FIG. 2 is a block diagram illustrating the configuration of the robot controller 10 according to the embodiment. FIG. 2 illustrates only components necessary for description of the present embodiment, and omits description of general components.

Also, in the description using FIG. 2, explanation will be made of mainly the internal configuration of the robot controller 10, and detailed explanation will be omitted regarding the host computer H and the controlled groups #1 and #2, which have already been illustrated in FIG. 1.

As illustrated in FIG. 2, the robot controller 10 is provided with a communication interface 10a, a common application program (AP) interface 10b, a storage unit 10c, a buffer 10d, and an execution control unit 10e. The robot controller 10 may further be provided with a display control unit 10f to be connected to a display device 20 such as a display.

The communication interface 10a is a communication device for the robot controller 10 to communicate with the host computer H. The common AP interface 10b is a software-implemented component for interpreting the instructions received from the host computer H via the communication interface 10a on a common platform.

When having received an instruction from the host computer H via the common AP interface 10b, the storage unit 10c holds the instruction until accepting an "issue" request for the instruction. Then, upon accepting the "issue" request, the storage unit 10c stores the instruction in the buffer 10d. The storage unit 10c may be notified of the issue request, for example, by turning on of an issue request flag separately provided in a temporary storage unit or the like.

Note that, for ease of explanation below, such storage of the instruction into the buffer 10d is assumed to be executed simultaneously for all of the controlled groups (here, #1 and #2). However, the time of storing the instruction may slightly differ between the controlled groups within the range of not affecting the coordinated operations. The storage unit 10c also stores therein, without any change, the "NOP" sent out from the host computer H to the controlled group that is not given a corresponding instruction stored at such storage time.

The buffer 10d is a storage area that temporarily stores therein, as the temporary storage unit, the instructions directed to the controlled groups #1 and #2. A data structure and so forth of the buffer 10d will be described in detail using FIGS. 3A and 3B.

When having accepted a predetermined operation request, the execution control unit 10e simultaneously fetches the instructions to the controlled groups #1 and #2 stored in the buffer 10d, one for each of the controlled groups at a time, and, based on the fetched instructions, makes the controlled groups #1 and #2 perform coordinated operations in synchronization with each other. Such an operation of the execution control unit 10e will be described in detail using FIGS. 4A to 7B.

Note that the predetermined operation request accepted by the execution control unit 10e may be given thereto, for example, by turning on an operation request flag separately provided in the temporary storage unit or the like. In this case, the execution control unit 10e sequentially fetches the instructions from the buffer 10d and makes the controlled groups #1 and #2 execute the instructions while the operation request flag is turned on.

The display control unit 10f displays contents of the buffer 10d on the display device 20. The contents of the buffer 10d displayed by the display control unit 10f will be described in detail by giving specific examples in FIGS. 8A and 8B.

Figure 3A:
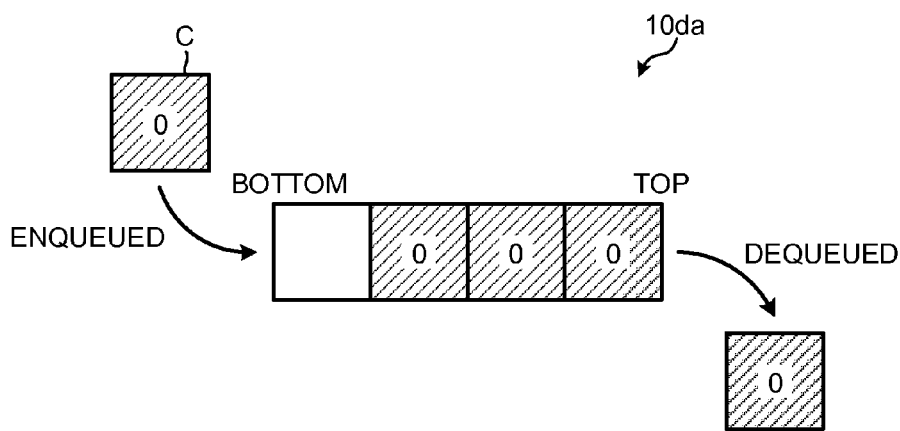
FIGS. 3A and 3B are schematic diagrams (No. 1) and (No. 2) illustrating details of a configuration of a buffer.
Figure 3B:
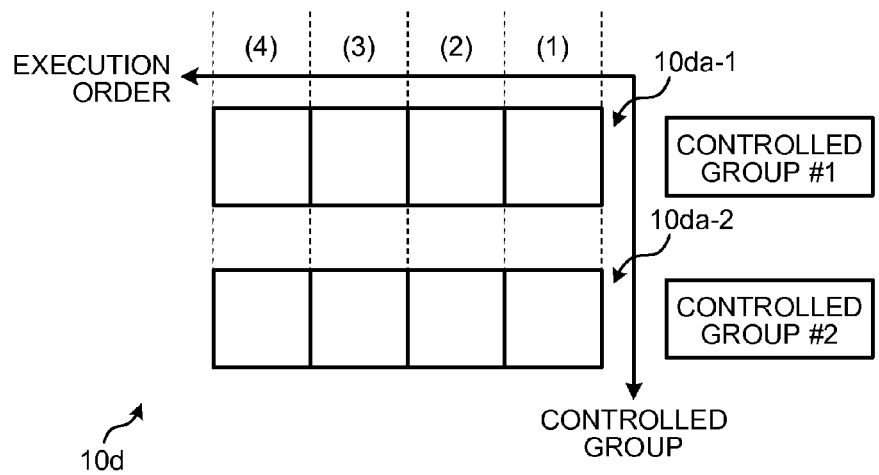

Next, details of a configuration of the buffer 10d will be described using FIGS. 3A and 3B. FIGS. 3A and 3B are schematic diagrams illustrating the details of the configuration of the buffer 10d.

As illustrated in FIG. 3A, the basic component unit of the buffer 10d is a queue 10da that is a so-called waiting queue. Specifically, the buffer 10d has a first-in first-out data structure in which a received instruction C is stored (enqueued), one at a time, from the bottom of the queue 10da, and is fetched (dequeued), one at a time, from the top thereof.

In the present embodiment, as illustrated in FIG. 3B, such queues 10da are provided for the controlled groups #1 and #2 as queues 10da-1 and 10da-2, respectively. While in the example of FIG. 3B, the queues 10da-1 and 10da-2 have the same number of elements, that is, four elements, the number of elements of the queue may differ among the controlled groups.

The above-described storage unit 10c simultaneously stores therein the instructions C to the controlled groups #1 and #2, one for each at a time, from the bottoms of the queues 10da-1 and 10da-2, respectively.

Here, as already described, the storage unit 10c stores therein the "NOP" as the instruction C to the controlled group that is not given the corresponding instruction C stored at such storage time. Accordingly, the instructions C (including the "NOP") stored at the same storage time are obviously given the same execution order illustrated in FIG. 3B.

Then, the above-described execution control unit 10e simultaneously fetches the instructions C to the controlled groups #1 and #2, one for each at a time, from the tops of the queues 10da-1 and 10da-2, respectively. In other words, the execution control unit 10e simultaneously fetches the instructions C (including the "NOP") that are stored at the same storage time and that are given the same execution order.

Then, the execution control unit 10e uses the instructions C that are simultaneously fetched and are given the same execution order to perform control (hereinafter mentioned as "execution control") to make the controlled groups #1 and #2 perform coordinated operations in synchronization with each other. Such operations of the execution control unit 10e will be described using subsequent FIGS. 4A to 7B. Note that the expression "in synchronization" refers to a state in which a plurality of robots simultaneously start operating and simultaneously stop operating. In contrast, a case in which a plurality of robots independently start operating and independently stop operating is expressed as "asynchronous".

Note also that the number "0" illustrated at the instruction C in FIG. 3A is a "task number" indicating a type of the instruction C. Such "task numbers" are used in the execution control performed by the execution control unit 10e. This point will also be described in the description using FIGS. 4A to 7B.

Figure 4A:
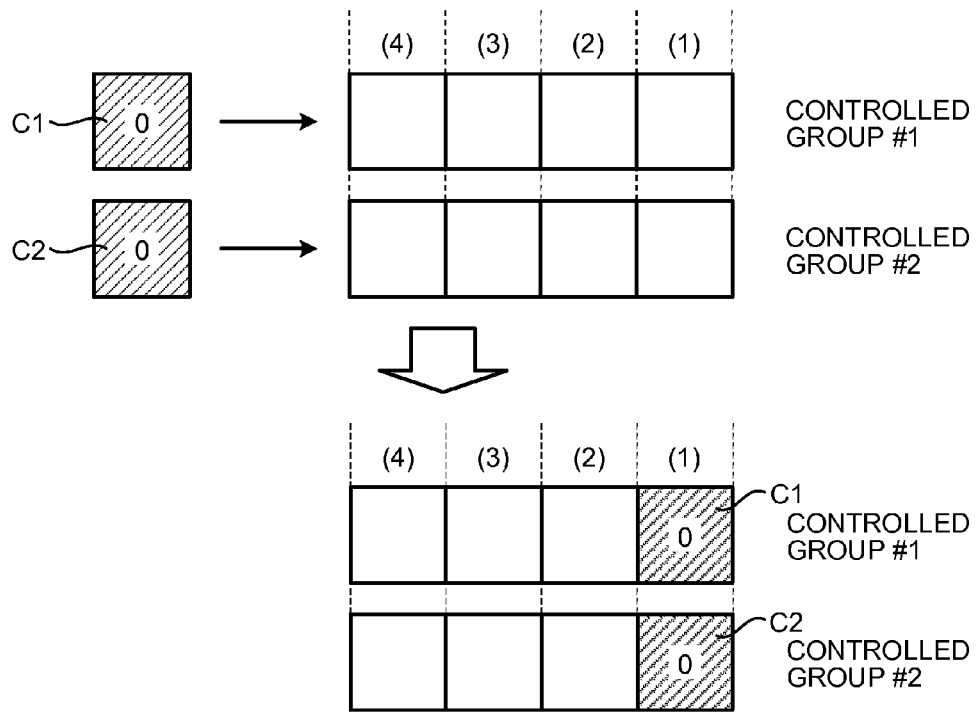
FIG. 4A is a diagram (No. 1) illustrating an example of a storage pattern of instructions.
Figure 4B:
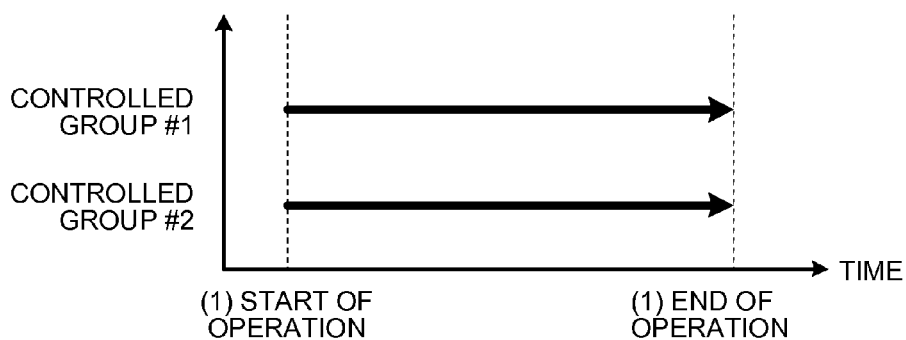
FIG. 4B is a diagram (No. 1) illustrating an example of execution control by an execution control unit.

FIG. 4A is a diagram (No. 1) illustrating an example of a storage pattern of instructions. FIG. 4B is a diagram (No. 1) illustrating an example of the execution control by the execution control unit 10e. Note that, in the drawings of FIG. 4A and later, from the viewpoint of ease of viewing, queues will not be attached with symbols such as 10da-1 or 10da-2, in some cases.

First, as illustrated in FIG. 4A, the storage unit 10c is assumed to store therein instructions C1 and C2, at the same storage time, from the bottoms of the empty queues 10da-1 and 10da-2, respectively, In such a case, the instructions C1 and C2 are stored in the queues 10da-1 and 10da-2 in the state of being aligned in the execution order (1). Note that, as illustrated in FIG. 4A, each of the instructions C1 and C2 is assumed to have the same task number of "0".

Here, the instructions C1 and C2 are assumed to be simultaneously fetched by the execution control unit 10e. The execution control unit 10e performs control so that all of the controlled groups simultaneously start the operations based on the simultaneously fetched instructions. The execution control unit 10e also performs control so that the controlled groups corresponding to the instructions having the same task number simultaneously stop the operations based on such instructions.

Specifically, as illustrated in FIG. 4B, the execution control unit 10e makes the controlled groups #1 and #2 simultaneously start the operations based on the simultaneously fetched instructions C1 and C2, respectively (refer to "(1) START OF OPERATION" in FIG. 4B).

Also, as illustrated in FIG. 4B, the execution control unit 10e makes the controlled groups #1 and #2 simultaneously stop the operations based on the instructions C1 and C2, respectively, having the same task number "0" (refer to "(1) END OF OPERATION" in FIG. 4B).

This means that both of the controlled groups operate in the same period of time even if one of them normally finishes the operation in a shorter time than the other. With this control, for example, in the case of intending to make two robots touch an object at exactly the same time, such as in the case in which the robot R1 and the robot R2 hold the object in a sandwiching manner from both side faces, an accurate coordinated operation can be performed.

Figure 5A:
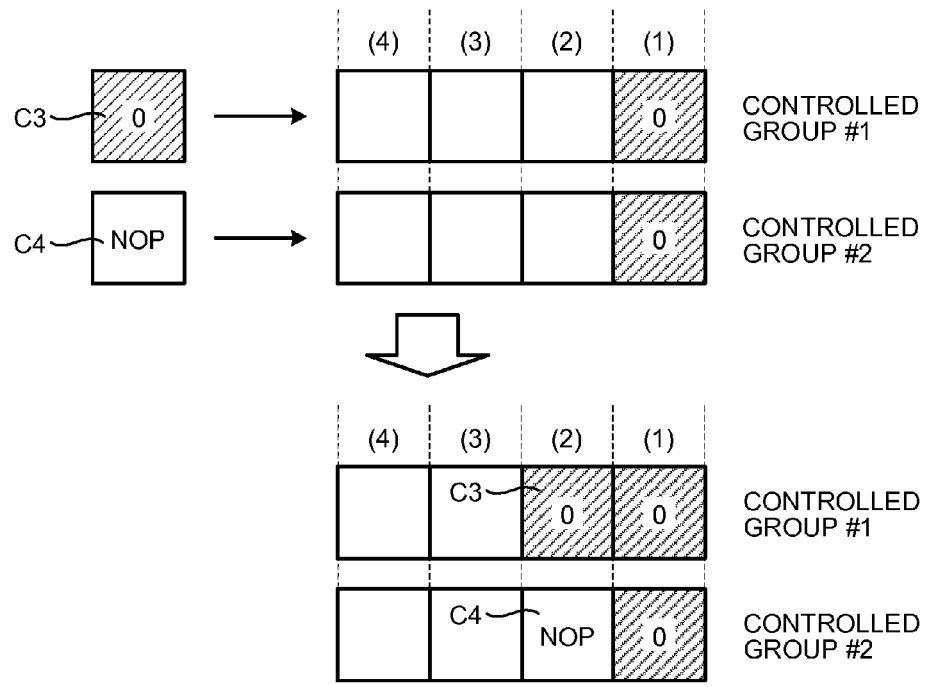
FIG. 5A is a diagram (No. 2) illustrating an example of the storage pattern of instructions.
Figure 5B:
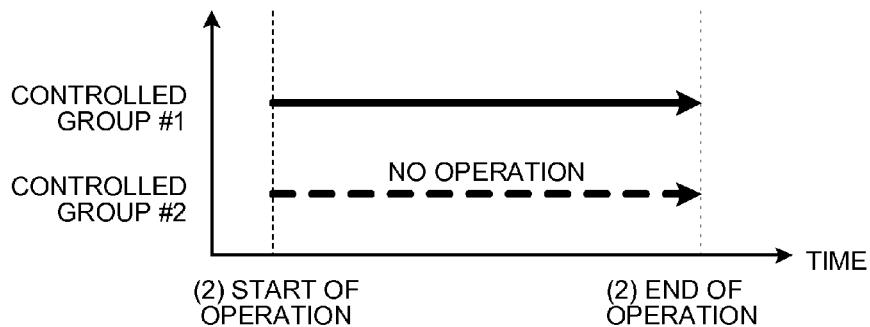
FIG. 5B is a diagram (No. 2) illustrating an example of the execution control by the execution control unit.

Next, FIG. 5A is a diagram (No. 2) illustrating an example of the storage pattern of instructions. In addition, FIG. 5B is a diagram (No. 2) illustrating an example of the execution control by the execution control unit 10e.

As illustrated in FIG. 5A, the storage unit 10c is assumed to store therein instructions C3 and C4, at the same storage time, from the bottoms of the queues 10da-1 and 10da-2, respectively, in each of which the position of the execution order (1) is already filled.

In such a case, the instructions C3 and C4 are stored in the queues 10da-1 and 10da-2 in the state of being aligned in the execution order (2). As illustrated in FIG. 5A, the instruction C3 is assumed to be a normal instruction having a task number "0", and the instruction C4 is assumed to be a "NOP".

Here, it is assumed that the instructions C3 and C4 are shifted to the tops of the queues 10da-1 and 10da-2, respectively, and are simultaneously fetched by the execution control unit 10e. If either of the fetched instructions is a "NOP", the execution control unit 10e performs control to keep the controlled group corresponding to the "NOP" from operating until the next instruction is fetched.

Specifically, as illustrated in FIG. 5B, the execution control unit 10e makes the controlled group #1 start an operation based on the instruction C3 out of the simultaneously fetched instructions C3 and C4 (refer to "(2) START OF OPERATION" in FIG. 5B).

In addition, as illustrated in FIG. 5B, the execution control unit 10e keeps the controlled group #2 corresponding to the instruction C4, that is, the "NOP", in the state of "no operation" until instructions are fetched next, that is, until the operation of the controlled group #1 based on the instruction C3 is terminated (refer to "(2) END OF OPERATION" in FIG. 5B).

With this control, the controlled groups can wait for each other to perform the operations. Therefore, the controlled groups can be synchronized and can accurately perform coordinated operations.

Figure 6A:
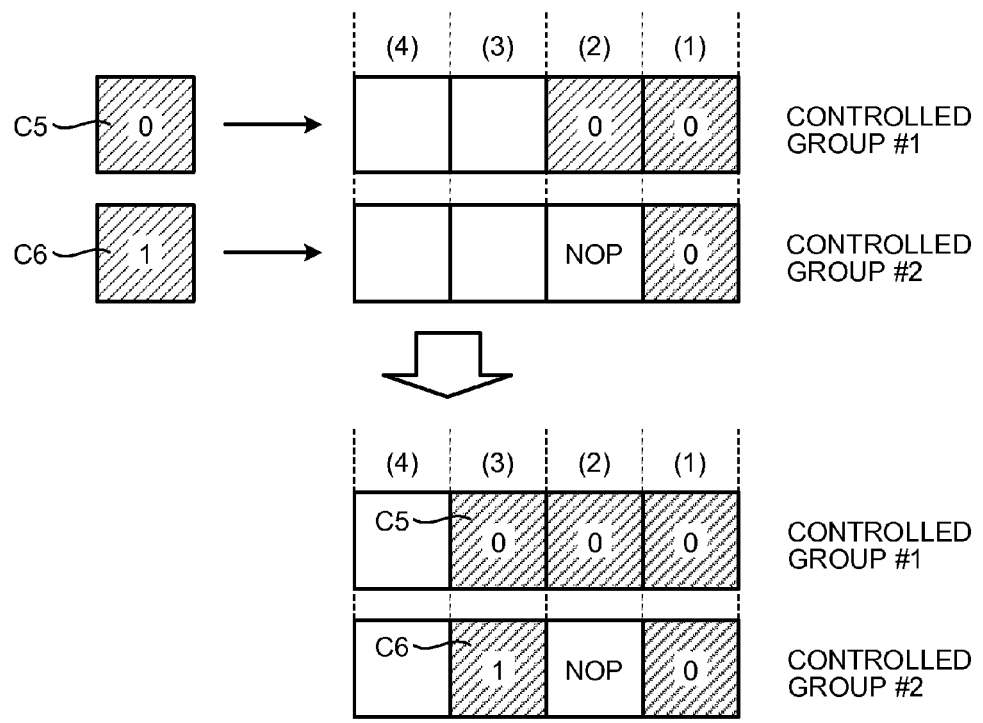
FIG. 6A is a diagram (No. 3) illustrating an example of the storage pattern of instructions.
Figure 6B:
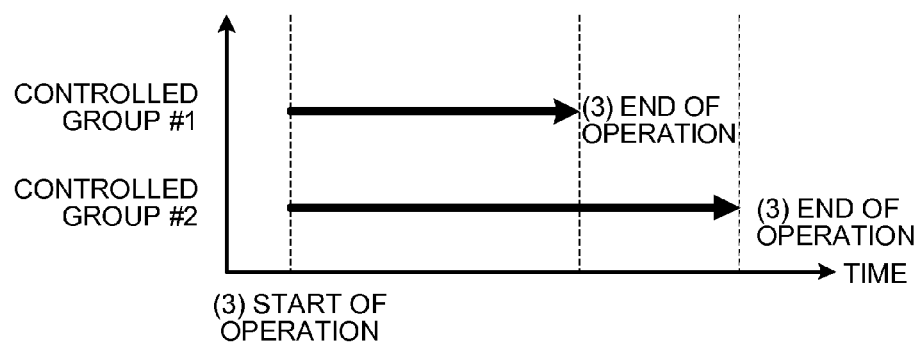
FIG. 6B is a diagram (No. 3) illustrating an example of the execution control by the execution control unit.

Next, FIG. 6A is a diagram (No. 3) illustrating an example of the storage pattern of instructions. FIG. 6B is a diagram (No. 3) illustrating an example of the execution control by the execution control unit 10e. In addition, FIGS. 6C to 6K are schematic diagrams (No. 1) to (No. 9) illustrating details of the execution control of the instructions. A series of processes of FIGS. 6C to 6K are also performed by the execution control unit 10e.

As illustrated in FIG. 6A, the storage unit 10c is assumed to store therein instructions C5 and C6, at the same storage time, from the bottoms of the queues 10da-1 and 10da-2, respectively, in each of which the positions of the execution orders (1) and (2) are already filled.

In such a case, the instructions C5 and C6 are stored in the queues 10da-1 and 10da-2 in the state of being aligned in the execution order (3). As illustrated in FIG. 6A, the instruction C5 is assumed to have a task number of "0", and the instruction C6 is assumed to have a task number of "1".

Here, description will be made, using FIGS. 6C to 6K, of a process in which the instructions C5 and C6 are shifted to the tops of the queues 10da-1 and 10da-2, respectively, and then executed. Note that each of outline arrows illustrated in FIGS. 6C to 6K indicates an instruction "to be executed", and the instruction indicated as "to be executed" is executed while the above-described operation request flag is turned on.

Figure 6C:
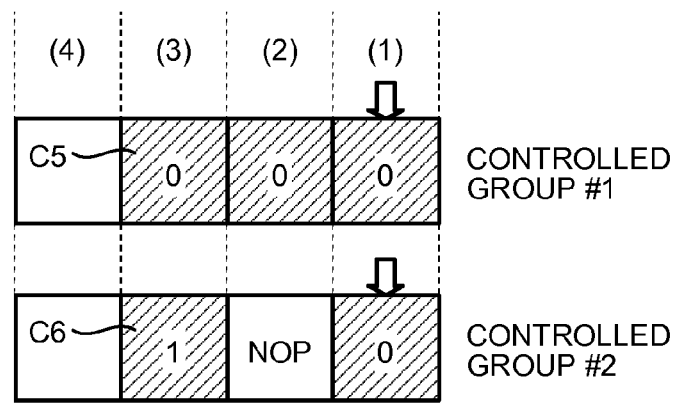
FIGS. 6C to 6K are schematic diagrams (No. 1) to (No. 9) illustrating details of the execution control of the instructions.
Figure 6D:
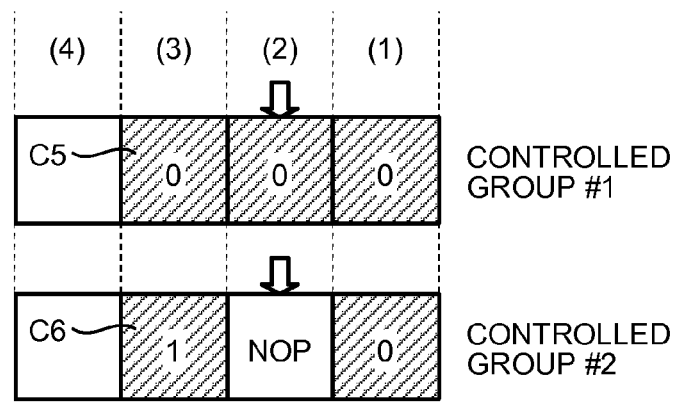

First, as illustrated in FIG. 6C, the instructions in the execution order (1) for both of the controlled groups #1 and #2 are set "to be executed". Because of having the same task number of "0", both of the instructions are executed and completed in synchronization with each other (simultaneous start and simultaneous stop), and the indications of "to be executed" are moved to instructions in the execution order (2) as illustrated in FIG. 6D.

Figure 6E:
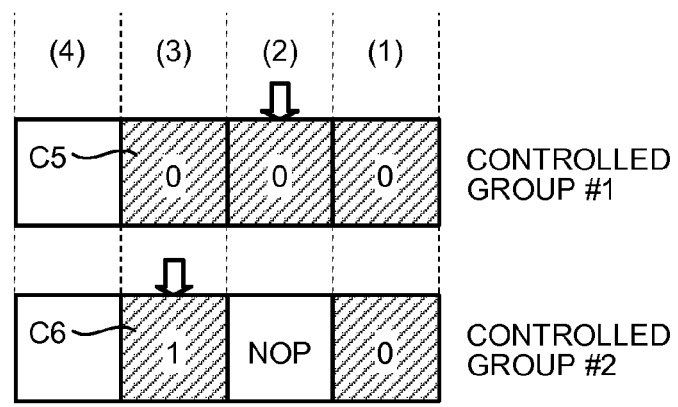

The instruction directed to the controlled group #2 is a "NOP" and thus cannot be "to be executed". Therefore, the indication of "to be executed" directed to the controlled group #2 is further moved to the instruction C6 in the next execution order (3), as illustrated in FIG. 6E. Here, although the instruction indicated by the indication of "to be executed" is in the execution order (3) for the controlled group #2, the indication of "to be executed" for the controlled group #1 still indicates the earlier execution order (2). Therefore, the instruction C6 is not executed immediately. The execution control unit 10e refers to contents of instructions for all other controlled groups in the same execution order as that of the instruction indicated by the indication of "to be executed", and, if an instruction other than a "NOP" is given to any one of the controlled groups and the instruction is not set "to be executed", waits until the instruction is set "to be executed".

Figure 6F:
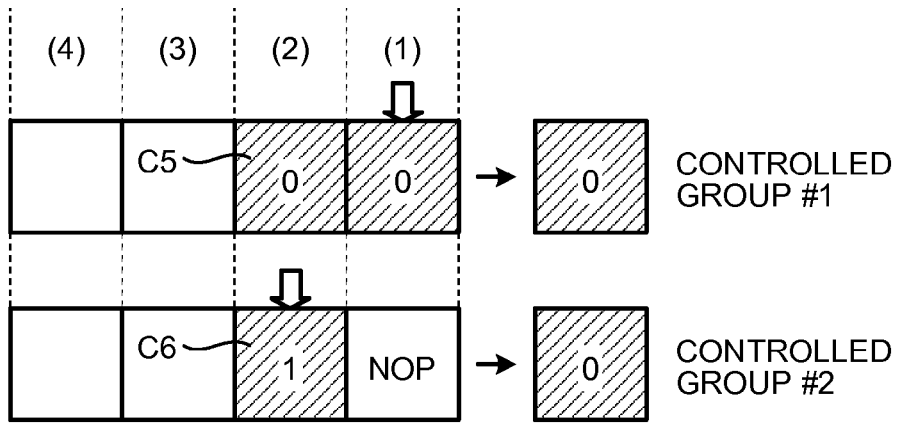

As illustrated in FIG. 6E, no instruction "to be executed" exists in the execution order (1) at this time point. Accordingly, as illustrated in FIG. 6F, the instructions at the tops of the queues 10da-1 and 10da-2 are dequeued both at a time, and the other instructions are moved forward.

Here, the queuing process will be described in detail using FIG. 6F as an example. First, for the controlled group #1, the indication of "to be executed" indicates the execution order (1). The instruction in the execution order (1) for the controlled group #2 is a "NOP". Accordingly, the controlled group #1 need not wait, and therefore executes the instruction in the execution order (1).

For the controlled group #2, the indication of "to be executed" indicates the execution order (2). The instruction (C5) other than a "NOP" exists in the execution order (2) for the controlled group #1, and the indication of "to be executed" for the controlled group #1 indicates the execution order (1). Accordingly, the instruction C6 for the controlled group #2 is not executed until the instruction C5 for the controlled group #1 becomes "to be executed", and thus, the execution control unit 10e waits until the instruction C5 becomes "to be executed". The flow chart of FIG. 6L illustrates this series of processes.

Figure 6G:
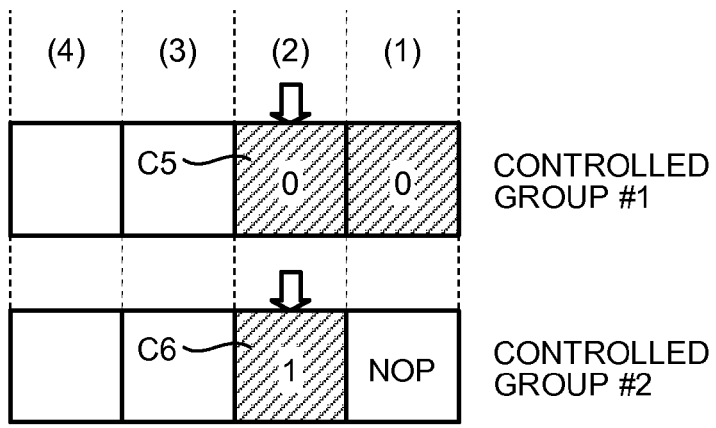
Figure 6H:
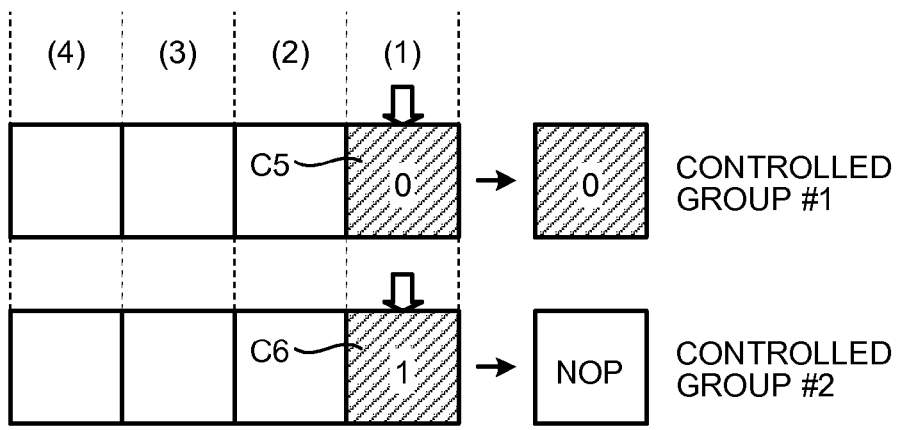
Figure 6I:
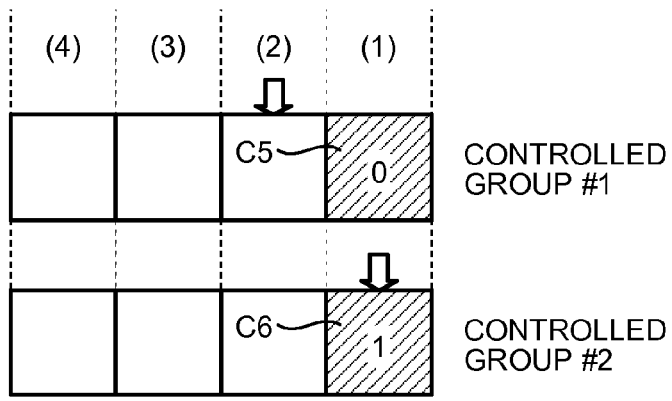
Figure 6J:
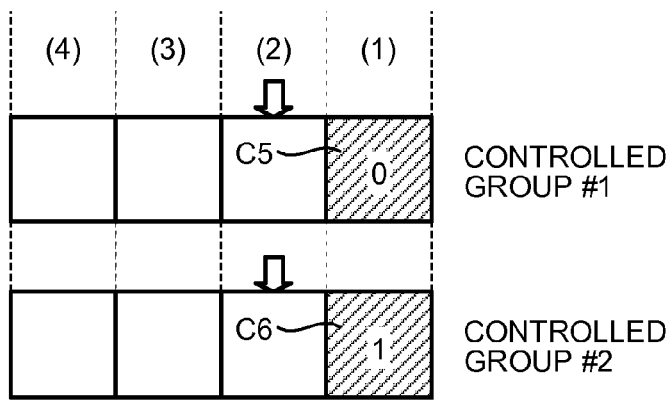
Figure 6K:
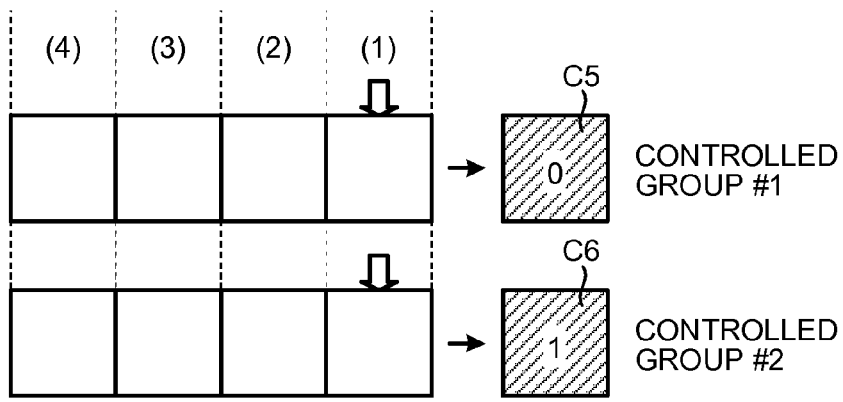
Figure 6L:
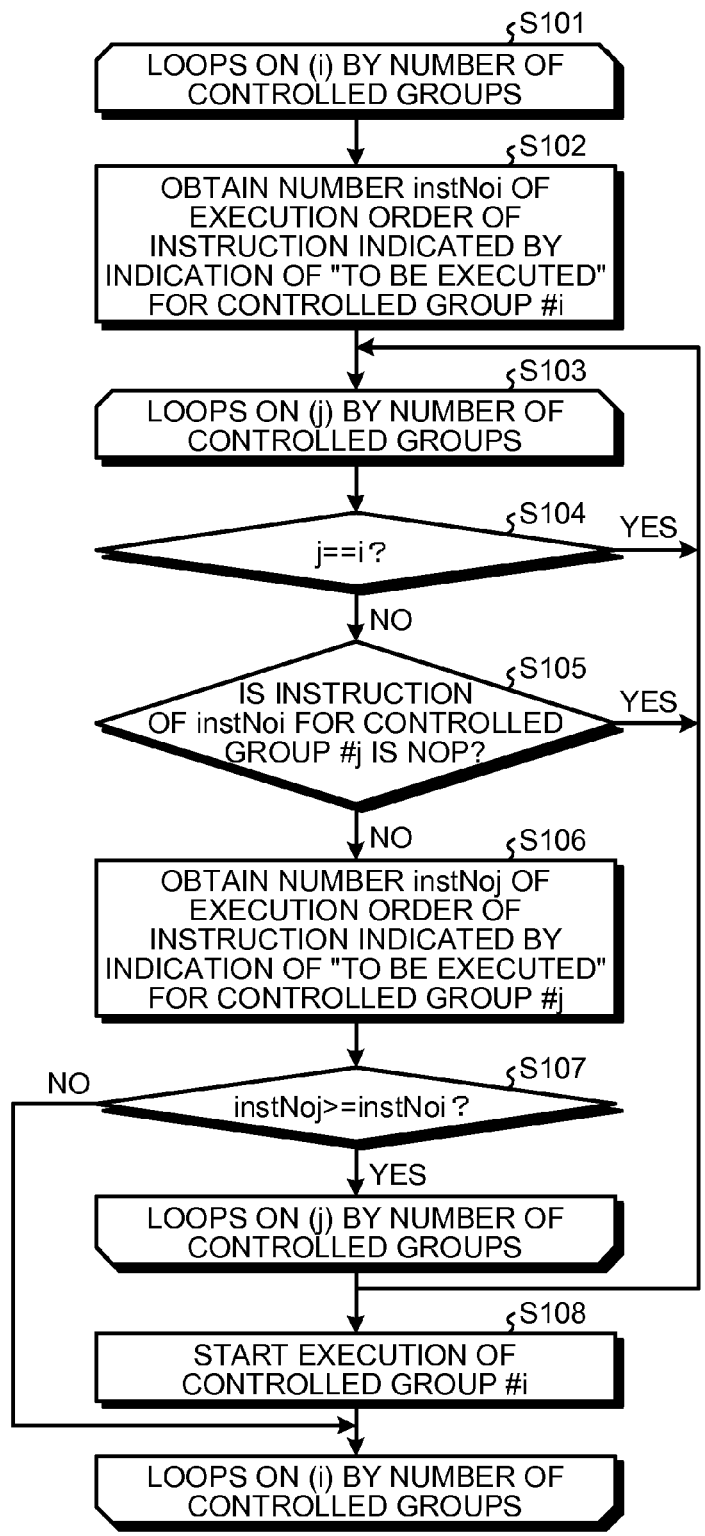
FIG. 6L is a flow chart illustrating a processing procedure of a queuing process.

Specifically, as illustrated in FIG. 6L, this series of processes are executed as a number of controlled groups of loop processes on (i), where a controlled group serving as a criterion is assumed to be a "controlled group #i" (Step S101). In the loop processes on (i), first, a number "instNoi" of the execution order of an instruction indicated by the indication of "to be executed" for the controlled group #i is obtained (Step S102).

Then, the controlled group #i is compared with another controlled group #j than the controlled group #i in a loop process on (j) (Step S103). In the loop process on (j), it is first determined whether j is equal to i (Step S104), and, if equal (Yes at Step S104), the controlled group #j is excluded as the controlled group #i. Specifically, the value of j is incremented by 1, and the process returns to a loop start of the loop process on (j).

If j is not equal to i (No at Step S104), it is determined whether the instruction of instNoi for the controlled group #j is a "NOP" (Step S105). If the instruction of "instNoi" for the controlled group #j is a "NOP" (Yes at Step S105), the condition for waiting cannot be met; therefore, the value of j is incremented by 1, and the process returns to a loop start of the loop process on (j).

Alternatively, if the instruction of "instNoi" for the controlled group #j is not a "NOP" (No at Step S105), a number "instNoj" of the execution order of an instruction indicated by the indication of "to be executed" for the controlled group #j is obtained (Step S106).

Then, the number "instNoj" is compared with the number "instNoi", and thus, it is determined whether the execution order of the controlled group #j is more advanced than that of the controlled group #i (Step S107).

If the determination condition of Step S107 is satisfied for all of the controlled groups #j (Yes at Step S107), the controlled group #i starts to be executed (Step S108).

Alternatively, if any one of the controlled groups #j does not satisfy the determination condition of Step S107 (No at Step S107), that is, if an instruction exists for the controlled group #j and the execution order thereof is earlier than that of the controlled group #i, an action of waiting for an instruction is performed for the controlled group #i.

Now, return to the explanation of FIG. 6F. After the instruction (task number "0") in the execution order (1) for the controlled group #1 is executed and completed in FIG. 6F, the indication of "to be executed" is moved to the instruction C5 in the execution order (2), as illustrated in FIG. 6G. Here, the instruction "to be executed" no longer exists in the execution order (1). Accordingly, as illustrated in FIG. 6H, the instructions at the tops of the queues 10da-1 and 10da-2 are dequeued both at a time in the same manner as illustrated in FIG. 6F, and the instructions C5 and C6 are moved forward.

Then, as illustrated in FIG. 6I, for the controlled group #1, the instruction C5 having a task number "0" is executed and completed, and the indication of "to be executed" is move to the next. Also, as illustrated in FIG. 6J, for the controlled group #2, the instruction C6 having a task number "1" is executed and completed, and the indication of "to be executed" is move to the next.

At this time, the execution control unit 10e does not perform control to stop operations based on the instructions having mutually different task numbers at the same time among the controlled groups corresponding to such instructions.

Specifically, as illustrated in FIG. 6B, although the execution control unit 10e starts the operations based on the instructions C5 and C6 at the same time for the controlled groups #1 and #2, respectively (refer to "(3) START OF OPERATION" in FIG. 6B), the execution control unit 10e does not control to stop the operations at the same time for the controlled groups #1 and #2. Therefore, the operations based on the instructions C5 and C6 may stop asynchronously with each other (refer to "(3) END OF OPERATION" of each group in FIG. 6B).

This means that, if one of the operations is finished in a shorter time than the other, one of the operations is independently stopped without spending the same time for both of the operations. With this control, the controlled groups can be operated in parallel without giving an unnecessary load to the system in situations in which operations need not be synchronized between the controlled groups, such as in the case in which the robot R1 and the robot R2 perform different operations from each other without a risk of interfering with each other.

Return to the explanation of FIG. 6J. As illustrated in FIG. 6J, the instruction "to be executed" no longer exists in the execution order (1) after the instructions C5 and C6 are executed and completed. Accordingly, as illustrated in FIG. 6K, the instructions C5 and C6 at the tops of the queues 10da-1 and 10da-2 are dequeued both at a time, and only the indications of "to be executed" are moved forward to be set at the tops of the queues 10da-1 and 10da-2.

Thus, the robot controller 10 according to the present embodiment can make the controlled groups perform the coordinated operations in accurate synchronization with each other by combining the execution control operations performed by the execution control unit 10e that have been described above using FIGS. 4A to 6K.

A specific example of such a combination is illustrated in FIGS. 7A and 7B. FIGS. 7A and 7B are diagrams (No. 1) and (No. 2) illustrating the specific example of the execution control in the robot controller 10 according to the embodiment.

Note that the specific example illustrated in FIGS. 7A and 7B discusses three controlled groups referred to as controlled groups #1 to #3. Note also that each symbol represented by an alphabetic character and an apostrophe or apostrophes, such as (a), (b)', and (d)", illustrated in FIGS. 7A and 7B indicates a "target position" targeted by each of the controlled groups at the time of operating according to one instruction.

For example, as illustrated in FIG. 7A, assume that the controlled group #1 is intended to perform an operation in which a control point corresponding to, for example, a point of application (portion to hold an object) of a hand mounted at a leading end of the robot follows a path from a current position thereof via (a), (b), and (c) to (d).

In a similar manner, assume that the controlled group #2 is intended to perform an operation in which a control point follows a path from a current position thereof via (a)', (b)', and (c)' to (d)'.

Also, in a similar manner, assume that the controlled group #3 is intended to perform an operation in which a control point follows a path from a current position thereof to (d)".

In addition, as indicated by outline arrows in FIG. 7A, assume that the operation of the controlled group #1 from (b) via (c) to (d) is intended to be synchronized with the operation of the controlled group #2 from (b)' via (c)' to (d)'. Furthermore, assume that the operation of the controlled group #1 from (c) to (d), the operation of the controlled group #2 from (c)' to (d)', and the operation of the controlled group #3 from the current position to (d)" are intended to be synchronized with each other.

Here, a specific example of the operations is as follows. First, while the robot R1 (controlled group #1) operates from the current position thereof to (b), the robot R2 (controlled group #2) operates from the current position thereof to (b)' independently from the robot R1. Thereafter, the robot R1 and the robot R2 hold both ends of the same object with the hands of both robots, and carry the object in a coordinated manner. Then, from halfway through the carrying, a robot R3 of the controlled group #3 applies processing to the object in synchronization with the movement of the object being carried.

In such a case, instructions only need to be stored in the queues 10da for the controlled groups #1 to #3 like the specific example illustrated in FIG. 7B. Specifically, instructions having different task numbers (here, "0" and "1") between the controlled groups #1 and #2 only need to be stored in each of the execution orders (1) and (2) so that the operations are performed asynchronously.

Further, instructions having the same task number (here, "0") between the controlled groups #1 and #2 only need to be stored in each of the execution orders (3) and (4) so that the execution control unit 10e performs control in a synchronous manner.

Furthermore, for the controlled group #3, a "NOP" as an instruction only needs to be stored in the execution orders (1) to (3) so as to prevent the controlled group #3 from performing waiting operation with the controlled groups #1 and #2. In addition, an instruction having the same task number of "0" as those of the controlled groups #1 and #2 only needs to be stored in the execution order (4).

Although FIGS. 7A and 7B illustrate the specific example in which the controlled group #3 operates from halfway in synchronization with the controlled groups #1 and #2 that are already in operation, the controlled group #3 can also be operated asynchronously. FIG. 7C illustrates such a specific example. FIG. 7C is a diagram (No. 3) illustrating the specific example of the execution control in the robot controller 10 according to the embodiment.

As illustrated in FIG. 7C, it is assumed that, in the execution orders (1) and (2), the controlled groups #1 and #2 are already placed in operation by instructions having a task number of "0". In this case, if an instruction is stored later (that is, as the execution order (3)) for the controlled group #3, and the instruction has an independent task number, such as "1" in FIG. 7C, the controlled group #3 starts operating asynchronously with the controlled groups #1 and #2 from the time when the instruction is stored.

Because a "NOP" is stored in each of the execution orders (1) and (2) for the controlled group #3 in FIG. 7C, the instruction stored in the execution order (3) is to be executed for the controlled group #3. This is also because a "NOP" is stored in the execution order (3) for the controlled groups #1 and #2, and thus the controlled group #3 need not perform waiting operation with the controlled groups #1 and #2.

In this manner, according to the present embodiment, in order to determine which controlled groups are to be synchronized with each other, it is only necessary to check whether the instructions in the same execution order in the queues 10da have the same task number. In other words, it is not necessary to make a search for task numbers of instructions stored in each of the queues 10da from the top of the queue 10da, but it is sufficient to compare task numbers between instructions having the same execution order. Therefore, even if the number of the controlled groups is increased, the synchronous control can easily be performed without complicating the processing.

Figure 8A:
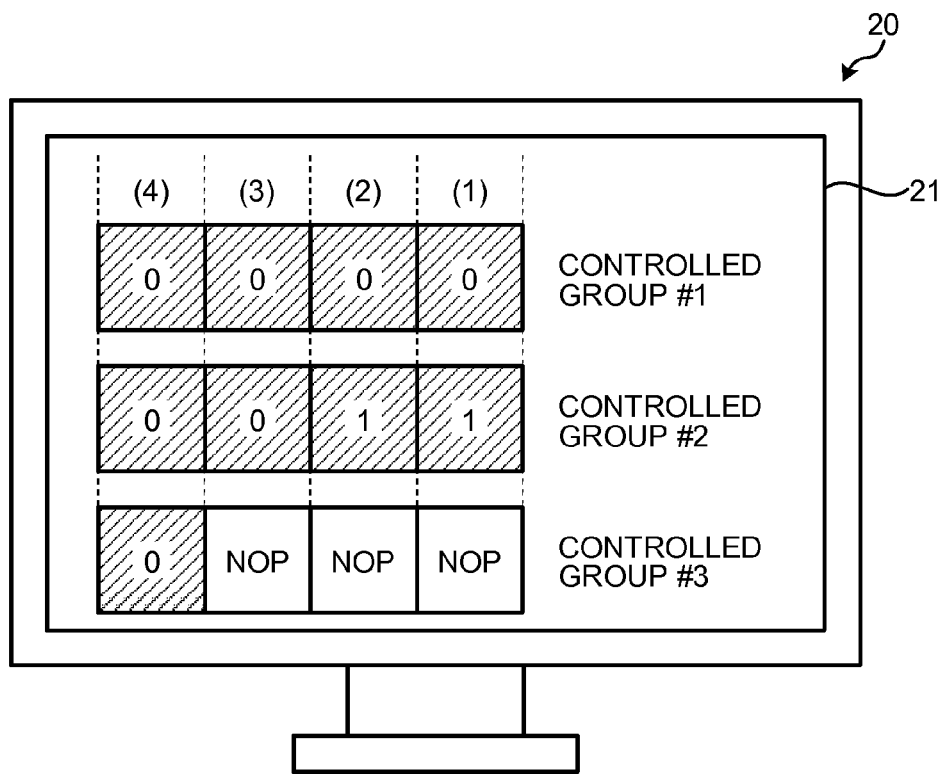
FIGS. 8A and 8B are diagrams (No. 1) and (No. 2) illustrating specific examples of contents of the buffer displayed by a display control unit.
Figure 8B:
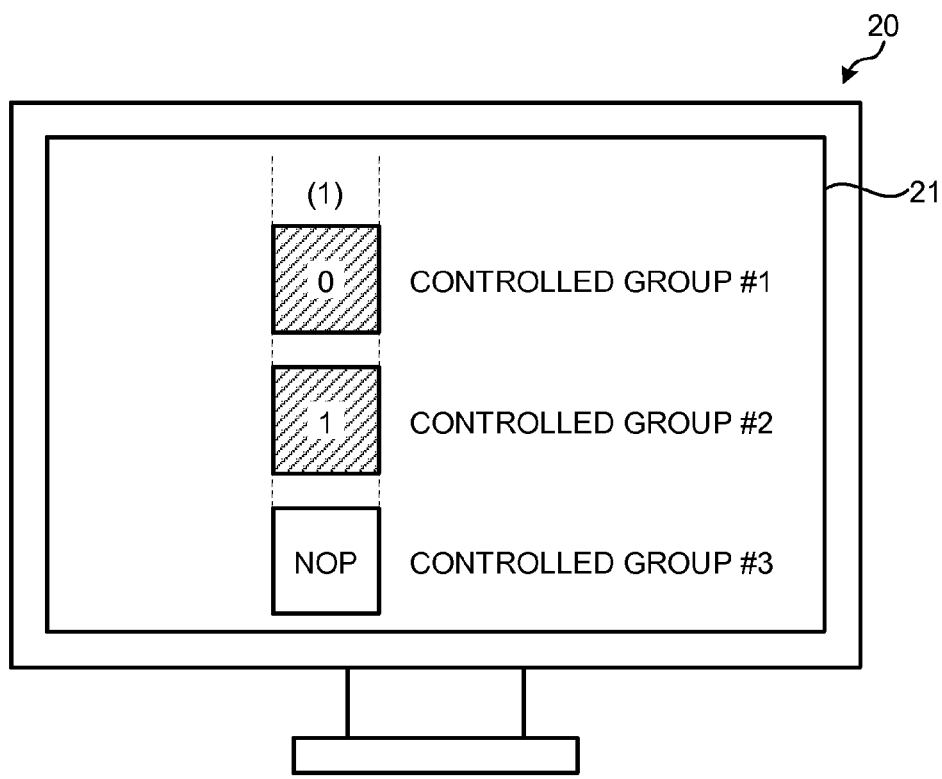

Next, description will be made, using FIGS. 8A and 8B, of specific examples of the contents of the buffer 10d (that is, the queues 10da) displayed on the display device 20 by the display control unit 10f. FIGS. 8A and 8B are diagrams illustrating the specific examples of the contents of the buffer 10d displayed by the display control unit 10f.

As illustrated in FIG. 8A, the display control unit 10f can display, for example, all of the instructions stored in the buffer 10d, in a display area 21 of the display device 20. At this time, a layout can be made so as to display texts such as (1) to (4) indicating execution orders together with texts such as "CONTROLLED GROUP #1" so that an operator actually viewing the display device 20 can easily check the contents of the buffer 10d.

The contents of the buffer 10d changing with time may also be displayed, for example, instead of as a still image, as a moving image such as an animation format image.

Alternatively, as illustrated in FIG. 8B, at least the instructions simultaneously stored in the queues 10da by the storage unit 10c may be arbitrarily narrowed down and displayed in the display area 21 of the display device 20. For example, FIG. 8B illustrates the specific example in which the contents are narrowed down to only instructions in the execution order (1) and displayed.

As a result, visibility can be improved for viewing current instruction execution states of the controlled groups and operations yet to be executed by them. Specifically, it is possible to find potential problems underlying in the robot system 1 at an early time and to debug the program. Thus, it is possible to improve reliability of the program and to perform more accurate synchronization and coordinated control.

As has been described above, the robot controller according to the embodiment is provided with the queues, the storage unit, and the execution control unit. Each of the queues is provided for each of the controlled groups serving as controlled units each including at least one axis of movement involved in the operation of the robot. The storage unit simultaneously stores therein the instructions directed to the controlled groups, one for each at a time, from the bottom ends of the queues therefor. When having accepted the predetermined operation request, the execution control unit simultaneously fetches the instructions directed to the controlled groups, one for each of the controlled groups at a time, from the tops of the queues therefor, and, makes all of the controlled groups simultaneously start the operations based on the instructions.

If there is any of the controlled groups to which no corresponding instruction exists at the time of storing the instructions, the storage unit stores therein a no-operation instruction as an instruction directed to such a controlled group. If the fetched instruction is the no-operation instruction, the execution control unit keeps the controlled group corresponding to the no-operation instruction from operating until an instruction is fetched next time. Therefore, with the robot controller according to the embodiment, the controlled groups can perform the coordinated operations in accurate synchronization with each other.

The above-described embodiment has illustrated, as an example, the case in which the robots included in the controlled groups are of the same type (all single-arm type), for example, as illustrated in FIG. 1. However, the embodiment is obviously not limited to those of the same type.

The above-described embodiment has also illustrated, as an example, the robot system having one host computer. However, the robot system may be configured, as a modification, to be provided with a plurality of host computers. Here, constitutional examples of such a case are illustrated in FIGS. 9 and 10.

Figure 9:
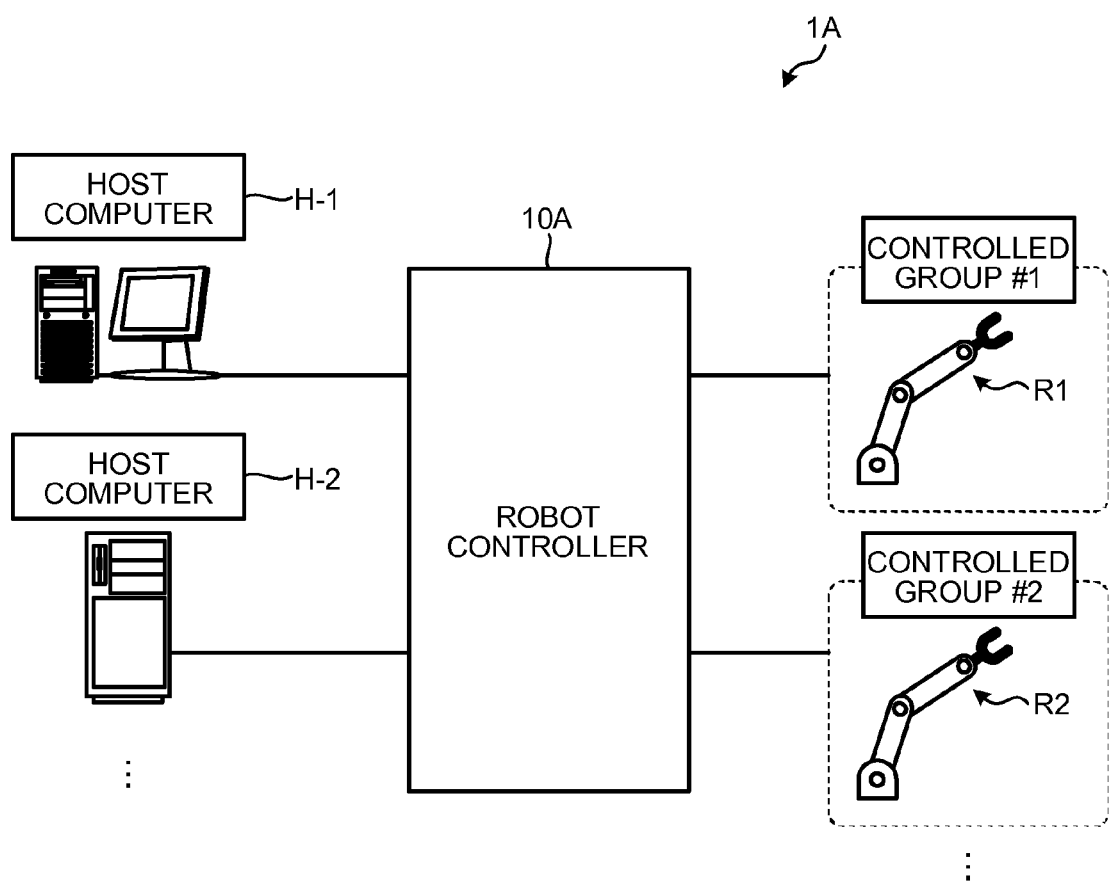
FIG. 9 is a diagram illustrating an overall configuration of a robot system according to a modification of the embodiment.
Figure 10:
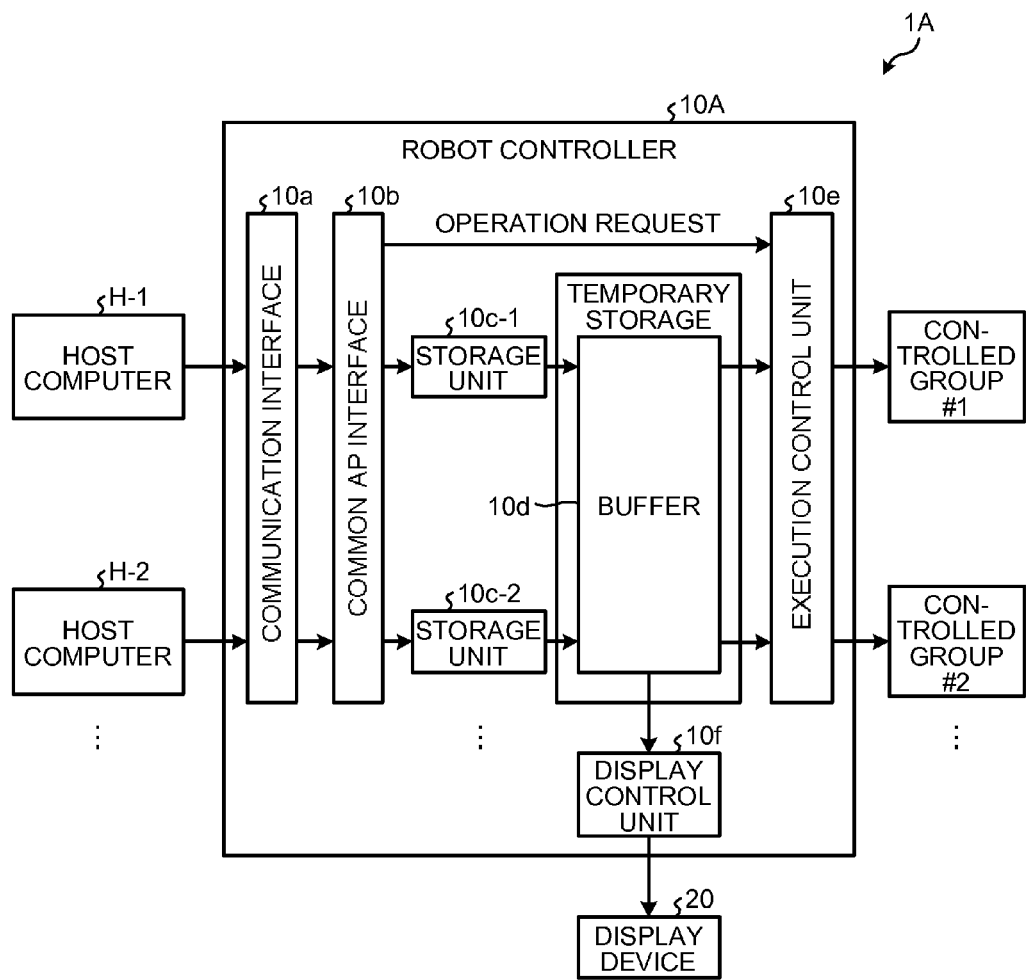
FIG. 10 is a block diagram illustrating a configuration of a robot controller according to the modification.

FIG. 9 is a diagram illustrating an overall configuration of a robot system 1A according to the modification of the embodiment, and FIG. 10 is a block diagram illustrating a configuration of a robot controller 10A according to the modification. FIGS. 9 and 10 correspond to FIGS. 1 and 2, respectively. Therefore, description of the duplicate components will be omitted, and different parts will mainly be described.

As illustrated in FIG. 9, the robot system 1A is provided with a plurality of host computers, the robot controller 10A, and, for example, the controlled groups #1 and #2. FIG. 9 illustrates at least two host computers H-1 and H-2 as an example.

The host computers H-1 and H-2 generate instructions directed to the controlled groups #1 and #2, and send out the instructions to the robot controller 10A. At this time, the host computers H-1 and H-2 can send out instructions to either of the controlled groups #1 and #2. In other words, the relationships between the host computers and the controlled groups are not limited to one-to-one relationships.

The host computers H-1 and H-2 can be configured on different platforms from each other. For example, the host computer H-1 may be composed of a PC, and the host computer H-2 may be composed of a PLC.

As illustrated in FIG. 10, the robot controller 10A is provided with a plurality of storage units 10c as storage units 10c-1 and 10c-2. When having received each of instructions from the host computers H-1 and H-2 via the communication interface 10a and then via the common AP interface 10b, each of the storage units 10c-1 and 10c-2 holds the instruction until accepting an "issue" request for the instruction, and, upon accepting the "issue" request, stores the instruction in the buffer 10d. Other components are the same as those of the robot controller 10 (refer to FIG. 2) according to the above-described embodiment, and therefore, description thereof will be omitted.

The above-described embodiment has also illustrated the example in which the queues are aligned vertically and horizontally in a two-dimensional array-like manner, for example, as illustrated in FIG. 3B. However, arrangement of the queues is not limited to this example. In other words, the queues may be arranged in areas secured in positions shifted from each other in the buffer.

The above-described embodiment has further illustrated, as an example, the case in which the number of elements of each the queues is four, for example, as illustrated in FIG. 3B. However, the number of elements may differ among the queues as described above, and is not limited to four.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A robot controller comprising:
    queues that are provided for respective controlled groups serving as controlled units each including at least one axis of movement involved in an operation of robots;
    a storage unit that stores therein instructions directed to the respective controlled groups, one at a time, from a bottom end of each of the queues; and
    an execution control unit that simultaneously fetches, when having accepted a predetermined operation request, the instructions directed to the controlled groups, one for each of the controlled groups at a time, from tops of the queues, and makes all of the controlled groups simultaneously start the operations based on the instructions; wherein
    the storage unit stores therein, if there is any of the controlled groups to which no corresponding instruction exists at the time of storing the instructions, a no-operation instruction as the instruction directed to the controlled group, and
    the execution control unit keeps, if the fetched instruction is the no-operation instruction, the controlled group corresponding to the no-operation instruction from operating until the instruction is fetched next time.

2. The robot controller according to claim 1, wherein
    the instructions each include a task number serving as a number indicating a type of the instruction; and
    the execution control unit makes the controlled groups corresponding to the instructions having the same task number simultaneously stop the operations based on the instructions.

3. The robot controller according to claim 2, wherein the execution control unit does not perform control to stop operations based on the instructions having different task numbers at the same time among the controlled groups corresponding to the instructions.

4. The robot controller according to claim 1, further comprising a display control unit that displays contents of the queues on a display device.

5. The robot controller according to claim 2, further comprising a display control unit that displays contents of the queues on a display device.

6. The robot controller according to claim 3, further comprising a display control unit that displays contents of the queues on a display device.

7. The robot controller according to claim 4, wherein the display control unit displays, on the display device, at least the instructions stored in the queues by the storage unit.

8. The robot controller according to claim 5, wherein the display control unit displays, on the display device, at least the instructions stored in the queues by the storage unit.

9. The robot controller according to claim 6, wherein the display control unit displays, on the display device, at least the instructions stored in the queues by the storage unit.

10. A robot system comprising the robot controller according to claim 1.

11. A robot controller comprising:

storage means for storing therein, one at a time, instructions directed to respective controlled groups serving as controlled units each including at least one axis of movement involved in an operation of robots, from a bottom end of each of queues that are provided for the respective controlled groups; and execution control means for simultaneously fetching, when having accepted a predetermined operation request, the instructions directed to the controlled groups, one for each of the controlled groups at a time, from tops of the queues, and for making all of the controlled groups simultaneously start the operations based on the instructions; wherein the storage means stores therein, if there is any of the controlled groups to which no corresponding instruction exists at the time of storing the instructions, a no-operation instruction as the instruction directed to the controlled group, and the execution control means keeps, if the fetched instruction is the no-operation instruction, the controlled group corresponding to the no-operation instruction from operating until the instruction is fetched next time.

* * * * *